(12) United States Patent
Pinedo et al.

(10) Patent No.: US 8,845,535 B2
(45) Date of Patent: Sep. 30, 2014

(54) DEVICE FOR DETECTING A MEDICAL CONDITION OR DISEASE

(75) Inventors: Herbert Michael Pinedo, Curacao (NL); Roderik Adriaan Kraaijenhagen, Amstelveen (NL); Albert Van Den Berg, Nijverdal (NL)

(73) Assignees: Herbert Michael Pinedo, Willemstad (CW); Roderik Adriaan Kraaijenhagen, Amstelveen (NL); Universiteit Twente, Enschede (NL)

( * ) Notice: Subject to any disclaimer, the term of this patent is extended or adjusted under 35 U.S.C. 154(b) by 688 days.

(21) Appl. No.: 12/918,790

(22) PCT Filed: Feb. 23, 2009

(86) PCT No.: PCT/NL2009/050081
§ 371 (c)(1),
(2), (4) Date: Nov. 5, 2010

(87) PCT Pub. No.: WO2009/104967
PCT Pub. Date: Aug. 27, 2009

(65) Prior Publication Data
US 2011/0046458 A1    Feb. 24, 2011

Related U.S. Application Data

(60) Provisional application No. 61/030,653, filed on Feb. 22, 2008.

(30) Foreign Application Priority Data

Feb. 22, 2008 (EP) .................................. 08151818

(51) Int. Cl.
*A61B 5/1455* (2006.01)
*A61B 5/145* (2006.01)
*A61B 5/07* (2006.01)
*A61B 10/00* (2006.01)
*A61B 5/00* (2006.01)

(52) U.S. Cl.
CPC .......... *A61B 5/07* (2013.01); *A61B 2562/0285* (2013.01); *A61B 10/0045* (2013.01); *A61B 5/145* (2013.01); *A61B 2010/0061* (2013.01); *A61B 5/0002* (2013.01); *A61B 5/14546* (2013.01)
USPC ........................................................ 600/309

(58) Field of Classification Search
USPC .................................................. 600/309–344
See application file for complete search history.

(56) References Cited

U.S. PATENT DOCUMENTS

| 5,823,954 | A | 10/1998 | Chaffringeon |
| 8,021,356 | B2 * | 9/2011 | Uchiyama et al. ......... 604/890.1 |
| 2002/0183721 | A1 | 12/2002 | Santini, Jr. et al. |
| 2004/0092825 | A1 * | 5/2004 | Madar et al. ................. 600/473 |
| 2005/0049472 | A1 * | 3/2005 | Manda et al. ................ 600/345 |
| 2005/0177069 | A1 * | 8/2005 | Takizawa et al. ............ 600/573 |
| 2008/0194912 | A1 * | 8/2008 | Trovato et al. .............. 600/118 |

FOREIGN PATENT DOCUMENTS

WO    WO 2007/113838 A2    10/2007
WO    WO 2008/012728 A1    1/2008

OTHER PUBLICATIONS

Hahm, Jong-In et al., "Direct Ultrasensitive Electrical Detection of DNA and DNA Sequence Variations Using Nanowire Nanosensors," Nano Letters, 2004, vol. 4, No. 1, pp. 51-54.
International Search Report mailed Apr. 21, 2009 in International Application No. PCT/NL2009/050081.

* cited by examiner

*Primary Examiner* — Eric Winakur
*Assistant Examiner* — Marjan Fardanesh
(74) *Attorney, Agent, or Firm* — Gilberto M. Villacorta; Sunit Talapatra; Foley & Lardner LLP

(57) ABSTRACT

The invention relates to a capsule or chip or sensor comprising a marker/detector and signalling device/method associated with the development of a medical condition/disease and to its use. This In Situ Lab On a Chip Signalling device (ISLOGS device) is used for detecting a medical condition/disease in situ or in vivo (inside the body), for example by swallowing it for testing in the digestive tract or by putting it into the vagina, mouth or nose. All reactions takes place in the body and when the test result is positive the device will notify the subject by colorizing the tested body fluid or biomaterial (for example faeces, urine or saliva) or the device itself. The detection is made outside of the body when the biomaterial or ISLOCS device has left the body.

27 Claims, 2 Drawing Sheets

DEVICE FOR DETECTING A MEDICAL CONDITION OR DISEASE

TECHNICAL FIELD

The invention relates to a capsule or chip or sensor comprising a marker/detector and signalling device/method associated with the development of a medical condition/disease and to its use.

BACKGROUND OF THE INVENTION

Medical knowledge on detecting and influencing disease processes have increased significantly in the last decennia. Advancing diagnostic technologies increasingly allow for earlier diagnosis and provide options for earlier and theoretically more effective treatment. Although most of the new advanced diagnostic methods are very useful to confirm a diagnosis in high risk individuals, they are, unfortunately, often still too costly and/or invasive and/or inconvenient and/or not specific enough (leading to false positive results, medicalization and increased healthcare costs) to provide to the general average risk population for early diagnostic and screening purposes. Therefore, new methods that can simplify the diagnostic procedure while maintaining high levels of sensitivity, specificity, minimal false-positive results and not being too costly are increasingly demanded. Furthermore, too improve the feasibility of diagnostic tests in a screening setting (to select those individuals for whom further (and more invasive) testing will be useful) they need to be as client/patient friendly, cheap and easy to use as possible. Each barrier, such as visiting a laboratory or medical centre, to have the test performed will influence the participation rate and is (cost-)inefficient. Empowerment of the individual with a trustworthy device that can be easily and safely used at home and that will only signal the subject if further action is needed, would be useful and efficient.

WO-A-2007/113838 discloses a swallowable device for detecting in vivo the presence of a condition. The device comprises a nanocontainer wherein a small amount of dye is received. As a direct result of detecting the condition, the small content of nanocontainers is released and a local colouring can be observed.

DETAILED DESCRIPTION OF THE INVENTION

The inventors came to the idea to combine different techniques reported over the last twenty years to detect and indicate the presence of a medical condition or disease in a subject using an automated miniature analysis system, also called a lab-on-a-chip (LOC) system or "smart pill" combined with a signalling method to notify a subject if a test result is "positive" (i.e. abnormal). The combination results in an "In Situ Lab On a Chip Signalling (ISLOCS) device". The ISLOCS device is small enough to be safely put internally into contact in a subject (gastrointestinal or vaginal contact for example), automatically analyzes samples in situ and notifies a subject if a "positive" result has been detected.

GENERAL DEFINITIONS

Within the context of the invention, a device of the invention is small enough to be safely put into a subject. Preferred dimensions of the device depends on the type of device used. For example, for an ingested device, preferred dimensions are comparable with the dimensions of a pill. More preferably, an ingested device has dimensions which range between approximately 5 mm and approximately 20 mm as illustrated in FIG. 2. More preferably, an ingested device has dimensions which range between 1 and 30 mm, more specifically between 5 mm and 20 mm. In another preferred embodiment, when a device is introduced into the vagina, dimensions may comprise between approximately 20 mm and approximately 50 mm. More preferably, when a device is introduced into the vagina, dimensions may comprise between 20 mm and 50 mm. In this application the device could for example be linked to a tampon which colorizes (i.e. blue) if the test result is "positive".

Within the context of the invention, "detecting" a medical condition or disease preferably relates to diagnosing, staging, monitoring, prognosticating or determining predisposition to a medical condition or disease.

Within the context of the invention, a subject is preferably a human or an animal. More preferably, a subject is a human.

Within the context of the invention, "in situ", means in a subject or in vivo.

Device

In a first aspect, the invention provides a device for detecting a medical condition or disease in a subject. The device is capable of entering the subject. The device comprises a detector which is able to specifically react in situ in a subject and to detect a marker associated with said medical condition or disease. The detection is executed under the condition of having entered the body of a subject. The detector is arranged and constructed to detect a marker after the device entering the body of a subject. The device will be received in a body fluid or biomaterial of a subject. At that location the detector will start 'searching' the marker, and will detect the marker if present. The device preferably comprises a signalling unit for emitting a visible substance, such as a coloured dye. The ejection of a sufficient amount of visible substance will colour a body fluid and will allow observation of the detection of the marker outside the body, when the bodily fluid exits the body.

The signalling unit will after detection of the marker emit the visible substance. The visible substance can be a colouring agent that colours a body fluid, said colouring being visible to the user or subject if the body fluid leaves the body. The detection is visualised by colouring e.g. a tested body fluid or biomaterial (for example faeces, urine or saliva) or the device itself, to notify the subject. The visualisation is visible for outsiders as the visible substance will leave the subject. The test results of the in situ detection will be visible from outside the subject. The visible substance can be a substance transportable by a body fluid and/or biomaterial.

The visible substance can be a coloured dye. The dye can be released upon detection of the marker. The device can have one, two or multiple chambers for receiving one or more dyes of different colours. The colours can correspond with predetermined markers. The dye corresponding with the detected marker is released upon detection. This allows detection of different markers using a single device.

In an embodiment, the device comprises a chamber or reservoir for a visualisable substance of at least 1 microliter to 100 microliter. Such a small amount suffices to be visible outside a subject.

In an embodiment the signalling device comprises a nanopump connected to the chamber and arranged for ejecting the visible substance from the chamber. A suitable nanopump system is known from Böhm, S., et al. (2000).

The device of the first aspect of the invention is described more extensively below and a most preferred embodiment thereof is also described (for detecting colorectal cancer).

In a first aspect, there is provided a device for detecting a medical condition or disease in a subject, wherein said device comprises a detector which is able to specifically react in situ in a body fluid or biomaterial of a subject and detect a marker associated with said medical condition or disease. The detector can send an actuation signal to a signalling unit. The signalling unit will upon receipt of the actuation signal emit and preferably eject the visualisable signal. The signalling unit can be arranged and constructed to emit a visible substance such as a dye having a predetermined colour. The detector can send a (detection) signal, preferably an electronic signal, to the signalling device upon detection. The detector and signalling device are electronically connected. By providing the detector or multiple detectors separate from the signalling unit, the signalling unit can be activated as a result of one or more conditions or e.g. with a delay after detection. Further multiple detections can be made and signal is only emitted after detection of a certain amount or combination of conditions.

In an embodiment the visible substance comprises a representation of the detected marker. In an embodiment the device is capable of detection multiple different markers. Detection of a specific marker leads to emitting of a specific visible substance. The emitted colour then represents the detected data. Multiple colours can be available. This allows the specific detection to be observed, visualised, outside the subject. The device can comprise multiple chambers wherein different visualisable substance are received, having different optical properties. Upon detection of a specific marker, a specific visualisable substance is released.

In an embodiment the visible substance can colour the device or part thereof, which will be visible once the device has left the body. In a preferred embodiment the coloured substance colours a body fluid or biomaterial that can leave the subject.

The device according to an embodiment comprises a house for entering a subject. This will allow the detector to react in situ for detecting a marker. Further such a house will allow the activation of the unit for visualising the detection of a marker. The house can be a capsule.

Preferably the device comprises a house for leaving a subject. This will allow the recovery of the device. There could also be a unit for visualisation located on the device that will indicate whether a marker was detected.

The device can comprise an electronic circuit. The device can be miniaturized. The device can be fabricated using methods commonly applied for the manufacture of integrated circuits, such as photolithography, reactive ion etching or electron beam evaporation.

In an embodiment the detector for detecting the marker comprises nanowires. As a result of detecting a marker, an electrical property, such as impedance, of a nanowire can change. The nanowires can be connected to a control circuitry, having an electrical power source. The nanowires and control circuitry form part of the detector of the device. The control circuitry can determine an electrical property of the nanowires, such as the impedance or resistance. The control circuitry is arranged to output an actuation signal at detection.

In a laboratory environment, nanowires can be calibrated by determining a threshold value that is an indication for detecting a targeted DNA molecule. This threshold value can be programmed in the control circuitry, e.g. in a memory. If during operation the threshold value is measured, the control circuitry can provide, output, an actuation signal.

Within the context of the invention, a medical condition or disease may refer to any disease or medical condition known to occur within a given subject, for which a specific detection system may be developed and incorporated into a LOC and for which said disease or medical condition is detectable in situ where a device has been introduced. Preferred diseases are cancer, for example gastrointestinal-, mouth/throat/salivary glands-, urogenital cancer, or Human Papilloma Virus infection, which may be a cervical infection and intestinal infections. In a preferred embodiment especially when an ingestible device is used, a medical condition or disease is a medical condition or disease of the digestive tract and/or detectable in the digestive tract. More preferably, medical conditions or diseases of the digestive tract are, amongst others, gastric- and duodenal ulcers with or without *H. pylori* infection, stomach cancer and colorectal cancer.

In another preferred embodiment, a medical condition or disease is a medical condition or disease of the vaginal tract and/or detectable in the vagina. Such medical condition or disease of the vaginal tract is preferably a cancer, preferably a HPV cancer and/or infection, or other infectious disease.

A device is first introduced in the mouth/swallowed or put internally into contact with a body fluid or biomaterial of a subject. In a first preferred embodiment, a device is an ingestible device like a pill. In this preferred embodiment, a device is ingested into a gastrointestinal tract of a subject and a detector of the device is able to specifically react in the digestive tract of a subject. In another preferred embodiment, a device is designed to be safely introduced into the vagina of a subject. In this other preferred embodiment, a detector present in a device is able to specifically react in the vaginal tract of a subject. In other embodiments, a device may be designed to be safely introduced into the anal tract, the mouth, the nose, the ear, or the eye of a subject. An example of a disease that may diagnosed via the mouth is mouth cancer, leukoplakie, caries or paradontitis. An example of a disease that may be diagnosed via the nose is nasopharyngeal carcinoma. Also for example the presence of Staphylococcus Aureus could be detected and visualized. A device of the invention is quite attractive since it does not necessitate the presence of a physician to carry out the detection of the medical disease or condition. The device is quite simple to use, may be used at home by a subject. There is no need to go to the doctor or to the hospital as long as the test result is normal.

Once the device is internally in contact with a subject, it may be needed that a device is resistant against degradation that could occur in situ. Preferably, when the device is an ingestible device, the device is resistant against degradation that could occur within the digestive tract. For example, said device may be resistant against stomach acid pH. Several enteric coating are already known and used in the formulation of medicaments. Examples of an enteric coating that may be present on a device may comprise gelatin and/or starch and/or cellulose and/or carrageenans and/or a polymer. Modified forms of starch and/or cellulose may also be used. Examples of polymers are impermeable hard polymers such as polypropylene and/or teflon.

In a preferred embodiment, a device of the invention comprises: a] an extraction unit and/or a purification unit for extracting and/or purifying a marker or a component present within a subject, b] a detector and c] means to transmit a signal to the outside world, e.g. comprising an emitter. The detected signal can be converted into a visualisable signal by ejecting a coloured substance. The ejected coloured substance, held in a reservoir in the device, will be mixed and dispersed in a bodily fluid, which bodily fluid can exit the body and will allow observation thereof outside the body. Each of these elements of the device are extensively described below.

In a preferred embodiment, a device comprises means to extract and/or purify a marker or a component present within a subject and whose detection will indicate that a medical condition or disease has been diagnosed. In a preferred embodiment means to extract and/or purify are present in a compartment of the device. A compartment indicates that this element is physically separated from other elements of the device. This may be realized by the use of an inert membrane. A preferred component to be extracted and/or purified is DNA. More preferred means to extract and/or purify among others DNA include a pump, mixing means, a liquid to be mixed with a sample extracted from a subject, an extracting column and/or a second distinct liquid. A preferred pump is a micromachined electrochemically driven pump capable of dosing precise nanoliter amounts of a liquid sample from a subject. Such pump consists of a micromachined channel structure realized in silicon by reactive ion etching (16). A liquid may facilitate the extraction and/or purification of a marker and/or component to be tested. A preferred liquid is a high salt solution. High preferably means about approximately 5 to 6 M salt solution. High preferably means between 5 and 6 M salt solution. More preferably, the salt is a chaotropic salt such as sodium iodide, sodium perchlorate and guanidine thiocyanate. A compound or marker present in a sample extracted from a subject may be diluted with a liquid present in a device of the invention. Subsequently, a purification may be carried out by passing a diluted sample from a subject on to an extraction column. An extraction column micromachined in glass or silicon is preferably a column designed to retain a marker and/or component to be detected. A retained marker and/or component may be subsequently released from a column by using a distinct second liquid. This second liquid may have a lower salt concentration than the one of the first liquid used. A released marker and/or component is preferably directed from the extraction column directly into a detector. In an even more preferred embodiment, the intestinal fluid is to be sampled, diluted and all free DNA is to be denatured in an initial step. The purification is then to be done based on the fact that DNA will bind to silica in the presence of high concentrations (about approximately 5 and 6M, or between 5 and 6 M) of chaotropic salt solutions, such as sodium iodide, sodium perchlorate and guanidine thiocyanate. These chaotropic salts are then washed away from the columns and system. The attached DNA is then released, or eluted, from the columns using a 10 mM-100 mM salt containing buffer solution or water. A preferred column is a silica column. Such columns are commercially available by Promega Corporation.

A centrifugation method may further be used to separate a marker from denatured proteins. The obtained supernatant may be subsequently delivered to an extraction column as defined herein. Ethanol precipitation may also be used as part of the extraction method.

A detector is a further element present in a device. A detector is able to specifically react in situ in a subject to detect a marker or component present in a sample extracted and/or purified from a subject. A detector has to be specifically designed depending on the medical condition or disease to be detected. A marker detected by a detector is known to be associated with said medical condition or disease. For example and as a preferred embodiment, when a cancer is to be detected, the presence or absence of a specific gene product associated with this cancer may be detected: for example the presence of an oncogene and/or the absence of a gene known to be a suppressor of tumour In this preferred embodiment, a detector comprises a probe or primer that is specifically able to recognize or hybridize with such a gene product such as mRNA, or protein. More preferably, a detector is able to specifically detect several types of diseases or medical conditions. Even more preferably, a detector is able to specifically detect several types of cancer. As an even more preferred embodiment, a detector is able to specifically detect a specific state of DNA. A preferred specific state of DNA in this context is hypermethylated DNA. Gene promoter hypermethylation is a specific marker for the development of several cancers ((9) till (15)). For detecting the presence of hypermethylated DNA, a detector preferably comprises a miniature silica extraction column with high surface area. "High surface area" refers to the fact that a porous structure is made in the glass material. This may be developed using conventional glass or silicon etching solutions. Such columns are commercially available as earlier defined herein.

In particular, the detector can comprise a control circuitry for analysis by comparison of detection results. In an embodiment the control circuitry measures and compares electric properties of the probe or primer, and if the property has a predefined value, determines that the marker is detected and outputs a actuation or detection signal to the signalling unit.

A device of the invention may stay inside a subject during a certain period of time. The duration of the period of time should be long enough to allow the extraction and/or purification and detection steps to take place. This period depends on the in situ localisation wherein a device has been introduced and the condition for which the device is used. For example, if a device has been introduced into the gastrointestinal tract by ingestion, the device will stay approximately one to three days in situ till it may be exported into the faeces. In this preferred embodiment, a device leaves a subject via his or her anal tract. For any other types of device for example intravaginal, the period of time may be much shorter and may be ranged between several minutes to a couple of hours. For this type of device, a subject will introduce the device and will take it out himself/herself. The duration of the period of time should be long enough to allow the extraction and/or purification and detection steps to take place.

Once a detection step has taken place, a signalling unit is actuated. In an embodiment means to convert a detection signal produced by the detector into a visualisable signal are present as a further element of a device. A signalling unit is arranged and constructed to emit a visible substance. In an embodiment upon detection of hypermethylated DNA the visible substance can be released. The conversion from detection to visualisable signal may be direct, i.e. in one single step. However, in a preferred embodiment, the conversion is realized in two steps or more by the presence of an electronic interface, which may translate a detection signal into an electronic signal which in its turn may be translated into a visualisable signal. A visualisable signal may be a colouring of the tested body fluid or biomaterial, for example faeces, urine or saliva or a colouring of the device itself, that can be detected by a human eye. The colouring of the tested body fluid or biomaterial is preferred due to practical and hygienic reasons. For example, a dye may be pulled out of a reservoir by a signal generated by the electronic signal emanating from an electronic interphase in response to a detection of a marker and/or compound. A visualisable signal may only be visualised once the device, body fluid or biomaterial has left a subject. This is not mandatory. The visualisable signal may already be theoretically visualised while the device is still in situ in a subject. However, this will generally not occur, since the visualisation with a human eye will only be possible once the device has left the subject. This language has been added to clarify that a device of the invention is not an imaging device.

In a preferred embodiment, a device is such that a detection is made without adding any other substance to a device once it has left a subject.

According to another aspect the invention provides a device for detecting a medical condition or disease in a subject. The device is capable of entering the subject. The device comprises a detector which is able to specifically react in situ in a subject and to detect a marker associated with said medical condition or disease. The detection is executed under the condition of having entered the body of the subject. The detector is arranged and constructed to detect a marker after the device entering the body of a subject. The device will be received in a body fluid or biomaterial of a subject. At that location the detector will start 'searching' the marker, and will detect the marker if present. The device preferably comprises a signalling unit for transmitting the detected data in some form to the outside world, such as via acoustic, optical, or radio frequency signals or a coloured dye.

According to the second aspect, there is provided a device for detecting a medical condition or disease in a subject, wherein the device comprises a detector which is able to specifically react in situ in a body fluid or biomaterial of a subject and detect a marker associated with said medical condition or disease. The detector comprises a control circuitry. As a result of detection, an electrical property, in particular the impedance or resistance of an element of the detector changes. The control circuitry can detect the change. The control circuitry can compare a change with a threshold value, e.g. available from a memory that is connected to the control circuitry. In dependence of the comparison of threshold value and electrical property, the control circuitry can provide an actuation signal for signalling that the marker is detected. According to the invention an actuation signal is formed due to the detection of a change in an electrical property of the detector. Preferably the detector comprises suitable nanowires.

A signalling unit is connected to the detector and specifically to the control circuitry. The signalling unit is arranged and constructed to emit a detectable signal, such as an acoustic, optical or RF signal, or a visible substance such as a dye having a predetermined colour, such that the detection is visualised outside the subject. The RF signal can be detected by an external receiver, or e.g. a cell phone and may be automatically transmitted to the expert's office. In an embodiment the acoustic signal, optical signal or visible substance will be observable once the device has left the body. In another embodiment the coloured substance colours a body fluid or biomaterial that can leave the subject.

In an embodiment of the nanowires are calibrated for detection of targeted DNA molecules. Calibrated nanowires can be connected to a control circuitry, said control circuitry having a memory with a parameter representing a threshold value for an impedance value of the nanowire. If the impedance of the nanowires changes and reaches said impedance during operation, this is a measure for identification of the targeted DNA molecules. Comparing the threshold value with the measured impedance in the nanowires using the control circuitry is a advantageous embodiment for detecting a marker.

In an embodiment the control circuitry is connected to a signaling device comprising a sound emitting unit for emitting sound after receiving an actuation signal from the control circuitry indicating detection of the targeted DNA molecule with the nanowire.

In an embodiment the signaling unit connected to the control circuitry comprises an electromagnetic radiation source, preferably an optical radiation source such as a visible light radiation source, that is operated to emit electromagnetic radiation as a result of receiving an actuation signal from the control circuitry. The electromagnetic emitter can be a radio frequency emitter for transmitting a detection signal through the body. Said signal can be received in a receiver outside the body. In an embodiment the signaling device comprises an ultrasonic sound emission unit.

In an embodiment a collection of differently calibrated nanowires is received in the capsule for detecting different DNA molecules. Detection of a DNA molecule results in an impedance/resistance change.

In an embodiment the emitted signal can comprise a code for identification of the targeted DNA molecule. The control circuitry sends an actuation signal representative for the detected marker/DNA molecule. The signaling device emits a signal comprising a code representative for the detected marker/DNA molecule. An operator is able to determine which targeted DNA molecule was detected. This allows detecting multiple different DNA molecules in a single "run".

A nanowire for detecting a targeted DNA molecule can be part of a microchip on the device. Such a microchip is known from Vrouwe (2005).

A Preferred ISLOCS Device for Detecting Colorectal Cancer

The situation of the diagnosis of colorectal cancer is representative for several relevant diseases in the western world, e.g. cardiovascular diseases, diabetes, kidney disease and various other cancers and is therefore exemplified below. Colorectal cancer is one of the most common malignancies that will be developed by at least 5% of the western population, and is considered one of the leading causes of cancer related death (1).

Fortunately, it is a disorder with a relatively long latent premalignant stage. This pathophysiology offers a clear 'window of opportunity' for early detection and effective treatment of the disease in an early phase. Colonoscopy is considered as the most effective method to detect the premalignant stage of colorectal cancer. This procedure, however, has several disadvantages, such as the large patient inconvenience, the possibility of serious complications and the high costs involved. There is, therefore, a broad consensus that colonoscopy should only be offered to individuals with an increased risk for colorectal cancer.

Based on current knowledge, Faeces Occult Blood Test (FOBT) is the most recognized method to select high risk individuals. Unfortunately, with FOBT a considerable percentage of the tumours in the screened group is missed. Consequently, there is need for further refinement of the selection methods preceding colonoscopy.

A new and exciting screening technique for colorectal cancer, as well as other types of cancers, is the detection of aberrant methylation, or hypermethylation, of normally unmethylated CpG islands of DNA (2,3). Methods for mapping methylated DNA regions have been demonstrated using Southern blotting hybridization assays (4), and methylation specific polymerase chain reaction (5). More recently, specific DNA methylation detection using microarray formats for sensitive, high throughput screening of patient samples has been reported (6).

Unfortunately, also these laboratory tests do not have a 100% accuracy. As a result they are preferably used as preselection method to select those individuals for whom further and usually more invasive testing will be useful. Especially in a screening setting the test need to be as client/patient friendly and easy to use as possible. Each barrier, such as visiting a laboratory or medical centre, to have the test performed will influence the participation rate and is (cost-)inefficient. A lab on a chip device that could be safely used at home and which only signals the user to go to the doctor if the test result is abnormal would be ideal in this setting.

Below we describe a most preferred device of the invention for detecting a colorectal cancer in the digestive tract of a subject. Upon ingestion, an ISLOCS device or smart pill travels to the intestines, where intestinal fluid is delivered to the ISLOCS device, which automatically extracts and purifies a DNA as earlier defined herein. A purified DNA sample is subsequently transported to a detection system where it interacts with a probe oligonucleotide molecule, specific for a particular methylation abnormality as defined above, said probe being immobilized directly on a sensor surface. If a DNA sample hybridizes with a probe, indicating a positive result, such event is directly detected electronically, and a colour-intense dye is expelled from a device, which will cover and penetrate a biological fluid/biomaterial, which is visualized when a subject defecates. This type of early warning disease detection may revolutionize methylated-related cancer diagnosis, treatment and, if successful, will drastically reduce cancer causing fatalities. The concept ISLOCS device may comprise many interacting components, but may be described best by outlining the five main system components: i) sample extraction and purification, ii) DNA detection, iii) electronic interfacing, iv) dye dosing positive detection notification and v) electrical power supply. A more extensive description of each component is given in the example.

Method

In a second aspect, there is provided a method for detecting a medical condition or disease in a subject wherein a device as defined in the previous section is used. The terms "detecting", "medical condition or disease" and "subject" have all been defined earlier herein. The method as defined herein is very attractive since it is a non-invasive method which could be carried out by a subject to be diagnosed. No collection or transport of the excreted biological fluid/biomaterial to a laboratory is required.

In this document and in its claims, the verb "to comprise" and its conjugations is used in its non-limiting sense to mean that items following the word are included, but combinations and/or items not specifically mentioned are not excluded.

In addition the verb "to consist" may be replaced by "to consist" essentially of meaning that a device, a part or a unit of said device or means present in said device as defined herein may comprise additional component(s) than the ones specifically identified, said additional component(s) not altering the unique characteristic of the invention.

The word "about" or "approximately" when used in association with a numerical value (about 10) preferably means that the value may be the given value of 10 more or less 1% of the value.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention is further illustrated by the following examples, which should not be construed for limiting the scope of the present invention.

BRIEF DESCRIPTION OF THE FIGURES

FIG. 1 shows a human subject 10. In the figure an exploded view of the human intestines 11 is shown. The subject 10 is ready to ingest an ISLOCS device.

FIG. 2 shows a preferred embodiment of the device 8 according to the invention. The device 8 is a ISLOCS device. The device 8 comprises 1 a battery, a sample extraction and treatment part 2, a detection part 3, a dosing part 4 and an electronics part 5. The device is encapsulated in a house 6. The device 8 can be swallowed. The detection part 3 is connected to a micro fluidic system comprising a tubing 18 and a micro pump 19, allowing to extract small amounts of bodily fluid into the housing of the device and through or along the detector. The detection part 3 is connected to the electronic part 5, comprising a control circuitry for measuring an electrical property of the detection part and allowing comparing the measured value with a threshold value, e.g. contained in a memory, also present in the electronic part 5.

Figure 1:
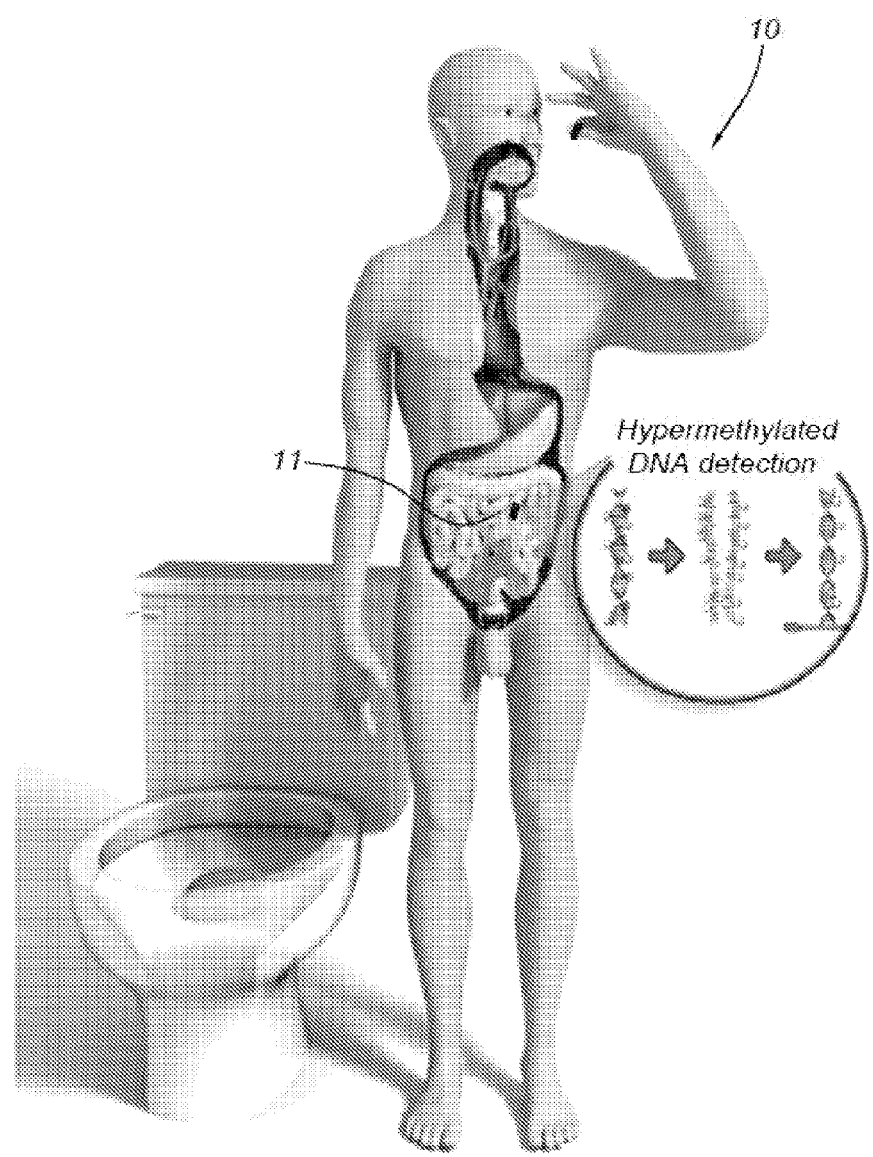
FIG. 1. Schematic representation of a subject.

The sample extraction and treatment part 2, the detection part 3 and electronics part 5 cooperate in order to take samples and detect the presence of a possible marker relating to a specific medical condition.

According to an aspect of the invention, detection of the marker results in a change in an electrical property of the detector, comprising the sample and treatment part 2, detection part 3 and electronics part 5. In an embodiment the electronics part 5 comprises a programmable memory and a compare module allowing comparing a current electrical property of the detection part, e.g. comprising nanowires, and a threshold value programmed in the memory. If the electrical property, such as the impedance of the detection part 3, reaches the threshold value, this is an indication for the fact that the marker is detected. Detection results in e.g. providing an actuation signal.

In an embodiment a detector comprises 1-1000 nanowires. The detector can be a part of a micro fluidic system. Small amounts of bodily fluids are pumped through the system and along the detector and in particular the nanowires.

The dosing part 4 is an example of a signalling unit for signalling and in particular visualizing a detected condition. The dosing part 4 can comprise a chamber filled with a dye fluid. If the detection part 3 detects a marker, the electronic part 5 will send a actuation signal to the signalling unit to trigger the dosing part, comprising e.g. a micro pump, to release the dye fluid. In an embodiment the dye fluid is released out of the housing 6 into the environment. If the device 8 is still inside the subject, the dye fluid will be released into a body fluid. The coloured body fluid will be visible to the subject 10 e.g. if the subject 10 uses a bathroom. In another embodiment the dye is released into the housing 6, which will take over the dye colour. The coloured housing 6 will be visible when the housing leave the subject 10.

In another embodiment the signalling unit comprises a device for emitting a signal to the outside world, other than a fluid release system. In an embodiment a RF signal is sent after detection of the marker. In an embodiment the device 8 comprises a (ultra)sound emitting source. The signalling device can be triggered by receiving the actuation signal from the detector.

In another embodiment the device 8 comprises a further housing part separate from the device. The device can be inserted in the human body using a separate insert e.g. for insertion into the vagina.

Figure 2:
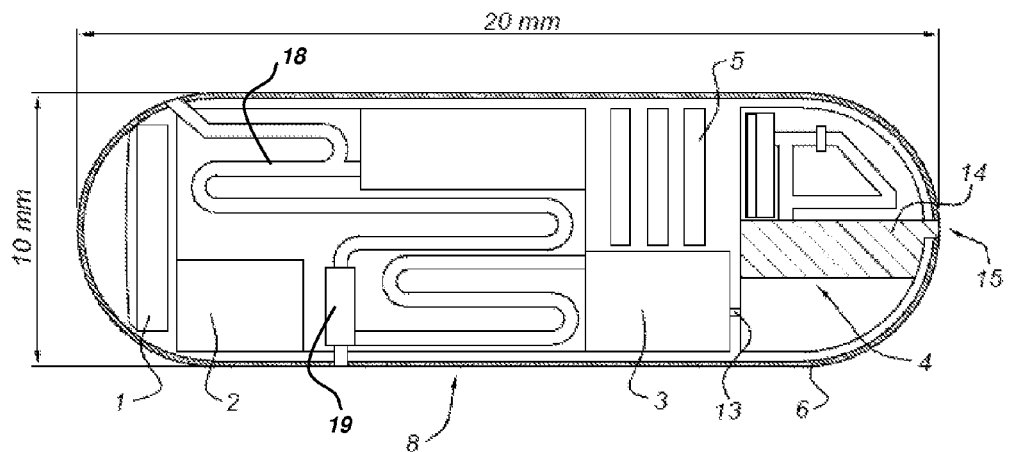
FIG. 2. Schematic representation of a first embodiment of the device according to the invention FIG. 3. Schematic representation of an output signal of a device according to FIG. 2.
Figure 3:
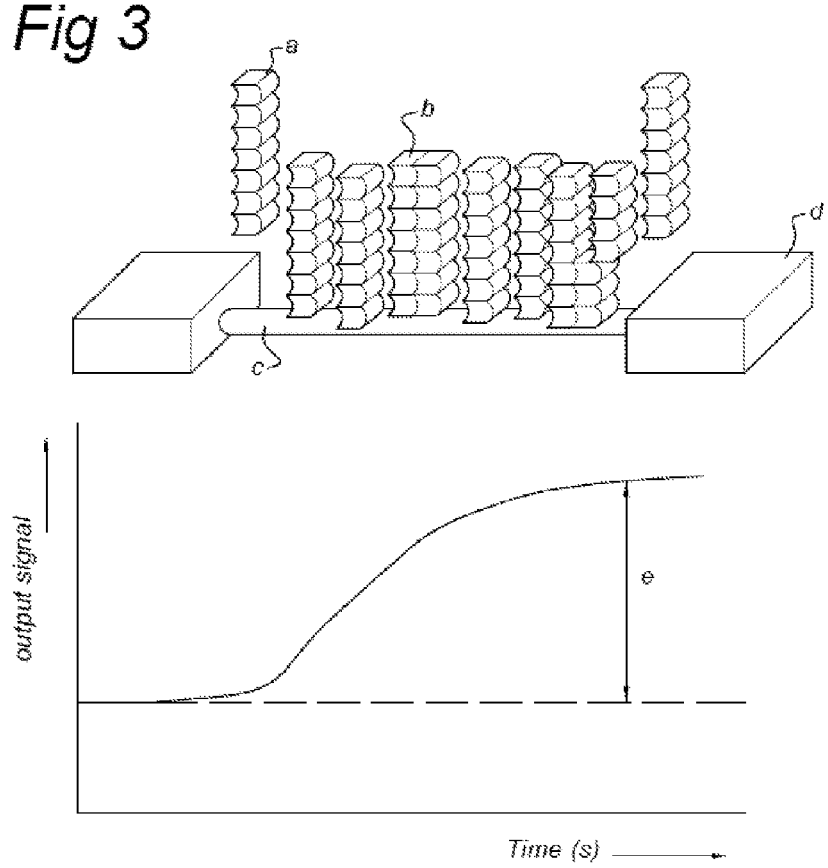

FIG. 3 shows a presentation of a signal from an ISLOCS device 8 according to FIG. 2. FIG. 3 shows detecting the state of methylation of the DNA of a subject: a represents the signal given for hypermethylated DNA, b represents the signal given for hybridized DNA, c is the nanowire sensor whereupon DNA may hybridize, d is the electrical terminal and e represents the signal change which is induced by hybridization of DNA to the nanowire sensor. The signal change may be a change of nanowire resistance, measured through the current that is transported through the nanowire at a given applied potential. The applied potential may be a direct-current (DC) voltage, or an alternating current (AC) with frequency from 0-1 GHz. The signal may also be the change in interfacial resistance between the nanowire surface and another electrode in contact with the DNA-sample solution. The resistance may be measured with DC or AC applied voltages, with a frequency range from 0-1 GHz. Fabrication of the nanowires is done using a combination of state of the art micro- and nanotechnologies, such as photolithography, E-beam lithography, laser-interference lithography, nanoimprint lithography, wet and dry etching, evaporation, sputtering, and e-beam implantation, to enable low price, high quality, low-contact resistance nanowire devices. After detection the signalling unit 4 is initiated to visualise the detection of the marker preferably by releasing the coloured substance/dye.

EXAMPLE

Blue Bolus Smart Pill System

The Blue Bolus smart pill is an ideal ISLOCS application, as most of the required system components can be realized with conventional technological methods. The basic operation of the Blue Bolus (BB) smart pill begins with a subject swallowing a pill. When the smart pill reaches the lower intestine, the pill begins to sample the intestinal fluid. The sample fluid is mixed with a pre-stored salt solution that purifies a DNA sample, which is subsequently captured with a miniature extraction column. The captured DNA molecules are then eluted from a column and transported to the detection element, which contains a probe molecule attached to a sensor surface. When a positive detection event occurs, then an integrated electronic commands that a blue, pre-stored dye is pumped out of the pill into the bowel, which can be easily observed after defecation. The complete operation of the smart pill is automated and controlled by the "brains" of the system, the electronic control chip. The subject swallowing the pill should not have diarrhea, but should take a stool softener on the same day as the smart pill and onwards till the stools appear 24-72 hours after taking the Smart Pill. This is to guarantee soft stools during the next 3 days and adequate mixing of the dye, if pumped out of the pill. The five primary BB smart pill system concepts are shown schematically in FIG. 2. The main functions of the smart pill, including sample extraction and purification, hypermethylated DNA detection, electronic interfacing, dye dosing notification and electrical power supply. Each of these system components are now described in more detail.

Sample Extraction and Purification

The intestinal fluid is sampled from the external environment of the ingested smart pill. The sampling of the intestinal fluid is to be performed with an integrated pump system (for example the micromachined electrochemically driven pump as described in (16)) capable of withdrawing an adequate amount of intestinal fluid and mixing with a high-salt solution (about approximately 5 and 6M of chaotropic a salt solution, such as sodium iodide, sodium perchlorate and guanidine thiocyanate). The ISLOCS device contains a miniature silica extraction column (silica column from Promega) with high surface area to capture the DNA directly from the diluted sample. The captured DNA is then released by flowing another pre-stored low-salt solution (same salt as before in a concentration ranged between approximately 10 mM-100 mM) through the column and directly to the detection assay.

DNA Detection

The purified DNA samples are transported directly to the detection system, which consists of an array of silicon nanowires (17) with oligonucleotide probe molecules attached to their surfaces. The probe molecules will be designed for a specific methylation abnormality, as has been reported for colorectal cancer (7), for example. Silicon nanowire sensors have been demonstrated to be highly sensitive to surface charge variations due to DNA/DNA hybridization and antibody/antigen binding. However, depending on the amount of hypermethylated DNA contained in the sample, then a pre-concentration step or sample amplification step, using an integrated polymerase chain reaction system, will be required at the expense of increase complexity. Specific polymerase chain reaction system have already been designed to specifically detect colon cancer in human stool DNA (18, 19). FIG. 3 shows a cartoon illustration of the DNA hybridization on the nanowire sensors and the resulting electrical output signal, which can be recorded directly by the integrated electronics. Silicon nanowires have recently been fabricated and electrically tested in the BIOS Group of the University of Twente (20). On the surface of the silicon nanowires the probe molecules will be immobilized using conventional silane linking chemistry. The probe molecules specific for a particular methylation abnormality will be tailored for this application.

Electronic Interfacing

The front-end of the electronics circuitry performs the acquisition of the nanowire signals by means of conventional measurement techniques. A low-power microcontroller, the "brains" of the system, keeps track of various functions in the pill such as timing, functional checks of the subsystems and the actual data processing. The output electronics consist of the dosing interface that starts or inhibits the actual dye dosing, depending on the microcontrollers evaluation of the nanowire response. The nanowires can be connected to a control circuitry comprising a comparing unit. The comparing unit can compare an electrical property of the nanowire with a set threshold. If the electrical property change enough, beyond the set threshold, this is a signal for the fact that the marker was detected. The change in the electrical property is a result of a chemical reaction of the marker and the nanowire. The threshold value can be provided in the control circuitry in a programmable memory. The threshold value can be provided as a result of a calibration test performed beforehand. One or more different nanowires can be present for detecting different markers. Different threshold values can be provided for allowing detection of different markers. One or more detection signalling units can be present in the device 8, each actuated with a different actuation signal by the electronic part 6, sending the signal as a result of a specific detection.

Dye Dosing Notification

The dye dosing function will be performed using a low-power electrochemical actuation technique. In this system the dye is pulled out of a reservoir by pressure generated by the electrolysis of water, a proven technique developed in the BIOS group (8). The dye dosing unit can comprise a nanopump connected to an electric source. A limited amount of dye fluid is present in a dye chamber. The volume per chamber can be up to 1 ml. In an embodiment multiple chambers filled with different dyes are available.

Electrical Power Supply

The electrical power for sample extraction, transportation, detection, electronic processing and dye dosing will be supplied by a commercial high energy density battery, which can easily provide enough energy for all functions and operations.

REFERENCES LIST

1. Jubb, A. M., et al. (2001) P. Methylation and colorectal cancer. J. Pathol. 195, 111-134.

2. Bird, A. (1986) CpG-rich islands and the function of DNA methylation. *Nature.* 321, 209-213.
3. Herman, J. G., et al. (1994) Silencing of the VHL tumor-suppressor gene by DNA methylation in renal carcinoma. *PNAS.* 91, 9700-9704.
4. Issa, J. P. et al. (1994). Methylation of the oestrogen receptor CpG island links ageing and neoplasia in human colon. *Nature Genet.* 7, 536-540.
5. Herman, J. G., et al. Methylation—specific PCR: a novel PCR assay for methylation status of CpG islands. *Proc. Natl. Acad. Sci. USA* 93, 9821-9826 (1996).
6. Rauch, T., et al. (2006). MIRA-assisted microarray analysis, a new technology for the determination of DNA methylation patterns, identifies frequent methylation of homeodomain-containing genes in lung cancer cells. *Cancer Res.* 66, 7939-7947.
7. Weber, M., et al. (2005). Chromosome-wide and promoter-specific analyses identify sites of differential DNA methylation in normal and transformed human cells. Nat Genet. 37, 853-862.
8. Böhm, S., et al. (2000). A closed-loop controlled electrochemically actuated. J. Micromech. Microeng. 10, 1-7.
9. Jubb A M, Bell Quirke P. Methylation and colorectal cancer, J. Pathol, 2005; 195(1):111-134
10. Kim Y H, Petko Z, Dziecatkowski S, Ghiassi M, Stain S, Chapman W C, Washington M K, Willis J, Markowitz S D, Grady W M. CpG island methylation of genes accumulates during the adenoma progression step of the multistep pathogenesis of colorectal cancer. Genes Chromosomes Cancer. 2006; 45(8):781-9.
11, Sato F. Meltzer S J. CpG island hypermethylation in progression of esophageal and gastric cancer.
Cancer. 2006; 106(3):483-93, Review.
12. Hoque M O, Begum S, Topaloglu O, Chatterjee A, Rosenbaum E, Van Criekinge W, Westra W E, Schoenberg M, Zahurak M, Goodman S N, Sidransky D. Quantitation of promoter methylation of multiple genes in urine DNA and bladder cancer detection. J Natl Cancer Inst. 2006; 98(14): 996-1004,
13. Wisman G B, Nijhuis E R, Hoque M O, Reesink-Peters N, Koning A J. Volders H H, Buikema H J, Boezen H M, Hollema H, Schuuring E, Sidransky D, van der Zee G. Assessment of gene promoter hypermethylation for detection of cervical neoplasia. Int J. Cancer. 2006 May 30; [Epub ahead of print]
14. Perry A S, Foley R, Woodson K, Lawler M. The emerging roles of DNA methylation in the clinical management of prostate cancer. Endocr Relat Cancer. 2006; 1392):557-77.
15. Hoque M O, Topaloglu O, Begum S, Henrique R, Rosenbaum E, Van Criekinge W. Westra W H, Sidransky D Quantitative methylation-specific polymerase chain reaction gene patterns in urine sediment distinguish prostate cancer patients from control subjects. J Clin Oncol, 2005; 23(27): 6569-75.
16. Böhm S et al: An integrated micromachined electrochemical pump and dosing system. (1999), Journal of Biomedical Microdevices, 1:121-130.
17. Jong-in Hahm et al: Direct ultrasensitive electrical detection of DNA and DNA sequence variations using nanowire nanosensors. (2004), Nano Letters, 4:51-54
18. Belshaw N J et al: Use of DNA from human stools to detect aberrant CpG island methylation of genes implicated in colorectal cancer. (2004), Cancer Epidemiology, Biomarkers & Prevention, 13:1495-1501
19. Hongzhi Zou et al: A sensitive method to quantify human long DNA in stool: relevance to colorectal cancer screening. (2006), Cancer Epidemiology, Biomarkers & Prevention, 15:1115-1119
20. Böhm S et al: A closed-loop controlled electrochemically actuated micro-dosing system. (2000), J. Micromech. Microeng., 10:498-504
21. Vrouwe E. X., Luttge R., Olthuis W., van den Berg A.; Microchip analysis of lithium in blood using moving boundary electrophoresis and zone electrophoresis (2005), ELECTROPHORESIS, 26:3032-3042.
22. E. Carlen and A. van den Berg, Nano Letters, (2008) accepted.

The invention claimed is:

1. A device for detecting a marker associated with a medical condition or disease in a subject, wherein the device is capable of entering the subject and comprises (a) a detector which is able to specifically react in situ to the marker present in a body fluid or biomaterial of the subject (b) a chamber wherein a visualisable substance is received, and (c) a signalling unit arranged and constructed to emit the visualisable substance from the chamber upon detection of the marker into the body fluid, the visualisable substance being visible outside the subject, wherein the device additionally comprises an extraction unit and/or a purification unit for extracting and/or purifying the marker from the body fluid or biomaterial of the subject.

2. The device according to claim 1, wherein the device further comprises a swallowable housing for entering a subject.

3. The device according to claim 1, wherein the device further comprises a housing for leaving a subject.

4. The device according to claim 1, wherein the detector comprises an automated miniature analysis system.

5. The device according to claim 1, wherein the signalling unit comprises a release mechanism for releasing the substance upon detection.

6. The device according to claim 1, wherein the visualisable substance is a dye.

7. The device according to claim 6, wherein the dye has a predetermined colour corresponding with the detection of a specific marker.

8. The device according to claim 1, wherein the visualisation of the detection is seen in a colouring of the body fluid or biomaterial which has been in contact with the device or in a colouring of the device itself.

9. The device according to claim 1, wherein the detector is able to specifically react in the digestive tract and/or vagina of a subject.

10. The device according to claim 9, wherein the device is an ingestible device and/or is resistant against degradation that occur within the digestive tract.

11. The device according to claim 1, wherein the medical condition or disease is a medical condition or disease of the digestive tract or vagina and/or detectable in the digestive tract or vagina.

12. The device according to claim 11, wherein the medical condition or disease of the vaginal tract is a HPV cancer.

13. The device according to claim 1, wherein the medical condition or disease of the digestive tract is a cancer, a colon cancer or a stomach cancer.

14. The device according to claim 1, wherein the subject is a human being.

15. The device according to claim 1, wherein the chamber has a volume of 1-100 microliter.

16. The device according to claim 1, wherein the device comprises two or more detectors for different markers.

17. The device according to claim 16, wherein upon detection of a combination of markers the signalling unit emits the visualisable substance.

18. The device according to claim 1, comprising multiple chambers, wherein a different visualisable substance is received in each of the chambers.

19. The device according to claim 1, wherein the detector comprises a control circuitry and a detecting element connected to the control circuitry, the detection element having an electrical property that changes if a marker is detected.

20. The device according to claim 19, wherein the detecting element comprises nanowires.

21. The device according to claim 19, wherein the control circuitry comprises a memory for a parameter representing a threshold value for the changing electrical property.

22. The device according to claim 21, wherein the electrical property is impedance.

23. A method for detecting a medical condition or disease in a subject, comprising: (i) administering to the subject a device according to claim 1; and (ii) determining whether the device has detected a marker associated with the medical condition or disease, wherein the presence of a visualisable substance is indicative of the medical condition or disease.

24. The method according to claim 23, wherein upon detection of the marker by a specific detector a specific visualisable substance is emitted from the chamber.

25. The method according to claim 23, further comprising (iii) removing the device from the subject.

26. The method according to claim 23, wherein the device is administered to the vaginal and/or anal tract.

27. A device for detecting a marker associated with a medical condition or disease in a subject, wherein the device is capable of entering the subject and comprises (a) a detector which is able to specifically react in situ to the marker present in a body fluid or biomaterial of the subject (b) control circuitry connected to the detector for measuring a change in the electrical impedance of resistance of the detector if a marker is detected, and (c) a signalling unit arranged and constructed to emit a signal upon detection of the marker which signal is detectable or visible outside of the subject, wherein the device additionally comprises an extraction unit and/or a purification unit for extracting and/or purifying the marker from the body fluid or biomaterial of the subject.

* * * * *